(12) United States Patent
Bandis

(10) Patent No.: US 9,269,935 B2
(45) Date of Patent: Feb. 23, 2016

(54) BATTERY PACK WITH INTEGRAL SEAL MEMBER AND ELECTRONIC DEVICE INCLUDING THE SAME

(71) Applicant: Varian Medical Systems, Inc., Palo Alto, CA (US)

(72) Inventor: Steven Douglas Bandis, West Jordan, UT (US)

(73) Assignee: Varian Medical Systems, Inc., Palo Alto, CA (US)

( * ) Notice: Subject to any disclaimer, the term of this patent is extended or adjusted under 35 U.S.C. 154(b) by 210 days.

(21) Appl. No.: 13/753,504

(22) Filed: Jan. 29, 2013

(65) Prior Publication Data

US 2014/0211921 A1    Jul. 31, 2014

(51) Int. Cl.
*H01M 2/08* (2006.01)
*H01L 27/146* (2006.01)
(Continued)

(52) U.S. Cl.
CPC ............ *H01M 2/1094* (2013.01); *A61B 6/4411* (2013.01); *H01L 27/14618* (2013.01);
(Continued)

(58) Field of Classification Search
CPC ....... H01M 2/00; H01M 2/02; H01M 2/0202; H01M 2/0207; H01M 2/021; H01M 2/04; H01M 2/0404; H01M 2/0408; H01M 2/0413; H01M 2/06; H01M 2/065; H01M 2/08; H01M 2/1016; H01M 2/1022; H01M 2/1094; H01M 2/14; H01M 2/18; H01M 2220/30; H04M 1/00; H04M 1/02; H04M 1/0202; H04M 1/0204; H04M 1/0249; H04M 1/0252; H04M 1/0254; H04M 1/026; H04M 1/0262; H04M 2001/0204; G06F 1/00; G06F 1/1633; G06F 1/1635; Y10S 224/902; Y10S 257/924; B29L 2031/3437; B29L 2031/3468; B29L 2031/7146; B29L 2031/3481; B29L 2031/712; A61B 6/4405; A61B 6/4411; A61B 6/4283; H01L 27/146; H01L 27/14601; H01L 27/14618; H01L 27/14658; H01L 27/14676; G01T 1/244
USPC ................ 378/98.8, 189–192, 204, 210, 102; 250/370.09; 439/345–346, 350–358, 439/367, 368, 370, 371, 366, 521, 522, 725, 439/729; 220/361–363, 523, 526–528
See application file for complete search history.

(56) References Cited

U.S. PATENT DOCUMENTS 5,354,625 A * 10/1994 Bentz et al. ................... 429/407
5,661,634 A *  8/1997 Obata et al. ............. 361/679.31
(Continued)

OTHER PUBLICATIONS

PCT, International Search Report and Written Opinion in PCT/US2014/013463, May 23, 2014, 11 pages.

*Primary Examiner* — Anastasia Midkiff
(74) *Attorney, Agent, or Firm* — Houst Consulting

(57) ABSTRACT

An electronic device employs a seal member to seal a battery pack to a housing member to prevent contaminants from entering into a battery bay. The electronic device includes a housing member having an exterior surface a portion of which defines a recess, an electronic assembly contained inside the housing member, and an battery pack received in the recess in the exterior surface of the housing member and electrically connected to the electronic assembly inside the housing member. The seal member engages the battery pack and the housing member along an outer circumference of the battery pack and an inner circumference of the recess such that the seal member seals the gap between the outer circumference of the battery pack and the inner circumference of the recess, thereby preventing contaminants from an external environment from entering into an interior of the recess through the gap.

22 Claims, 7 Drawing Sheets

(51) Int. Cl.
   *H01M 2/10* (2006.01)
   *A61B 6/00* (2006.01)
   *H01M 2/02* (2006.01)
   *G06F 1/16* (2006.01)
   *B29L 31/00* (2006.01)

(52) U.S. Cl.
   CPC ............... *H01M2/08* (2013.01); *A61B 6/4283* (2013.01); *A61B 6/4405* (2013.01); *A61B 6/56* (2013.01); *B29L 2031/7146* (2013.01); *G06F 1/1635* (2013.01); *H01M 2/0202* (2013.01); *H01M 2/0207* (2013.01); *H01M 2/1022* (2013.01); *H01M 2/1066* (2013.01); *H01M 2220/30* (2013.01); *Y10S 224/902* (2013.01); *Y10S 257/924* (2013.01)

(56) References Cited

U.S. PATENT DOCUMENTS

| | | | |
|---|---|---|---|
| 5,704,803 A | 1/1998 | Oshima et al. | |
| 6,921,089 B2 | 7/2005 | Groh et al. | |
| 7,003,356 B2 | 2/2006 | Tsukamoto et al. | |
| 7,556,442 B2 | 7/2009 | Frantz et al. | |
| 2003/0170531 A1* | 9/2003 | Bean et al. | 429/65 |
| 2009/0016418 A1* | 1/2009 | Silver et al. | 375/220 |
| 2009/0240245 A1* | 9/2009 | Deville et al. | 606/33 |
| 2010/0284521 A1* | 11/2010 | Mcbroom et al. | 378/189 |
| 2010/0308991 A1* | 12/2010 | Adams et al. | 340/539.12 |
| 2011/0070472 A1* | 3/2011 | Cui et al. | 429/97 |
| 2012/0114998 A1* | 5/2012 | Hwang | 429/99 |
| 2012/0150248 A1 | 6/2012 | Chi et al. | |
| 2013/0209866 A1* | 8/2013 | Watanabe | 429/163 |

* cited by examiner

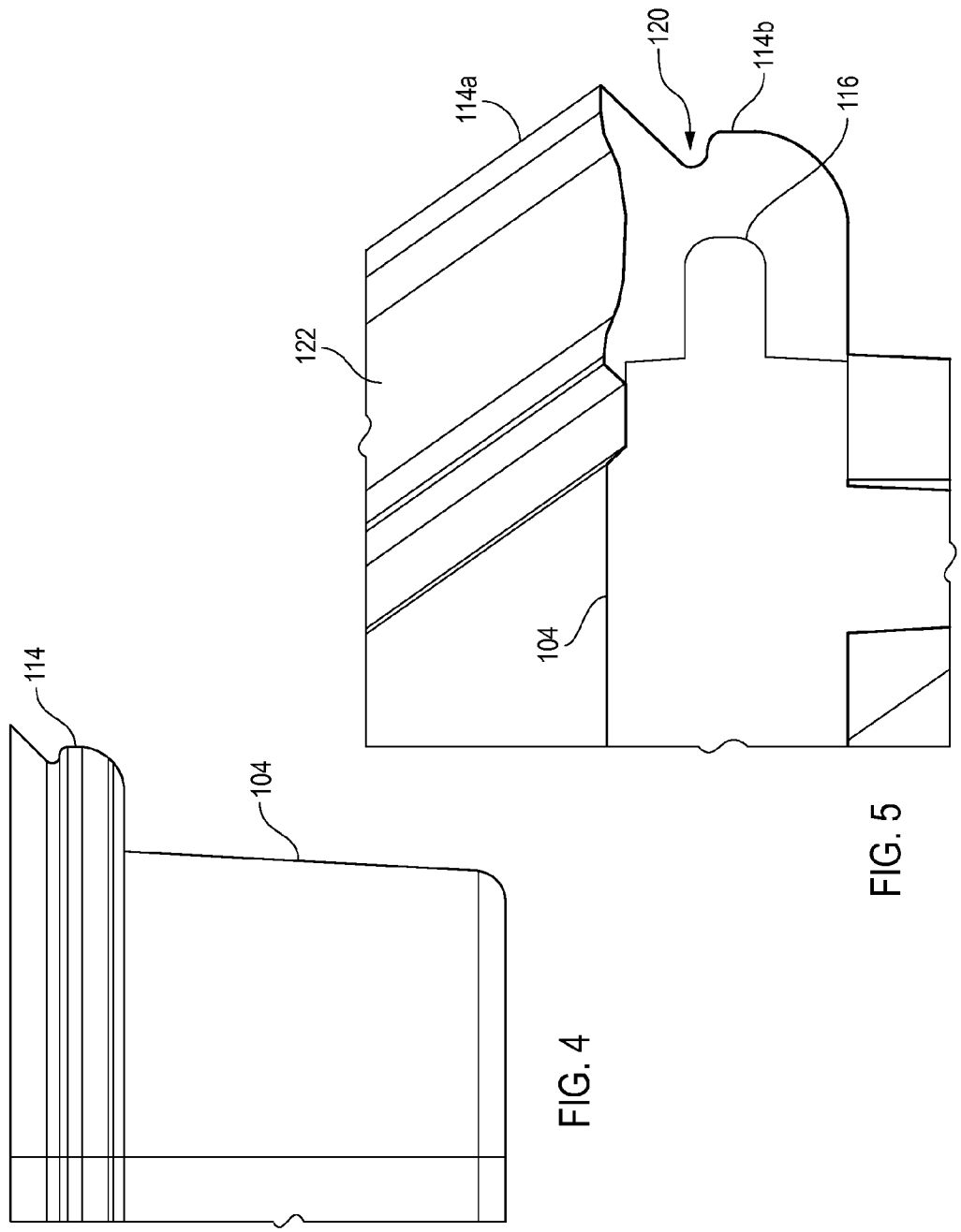

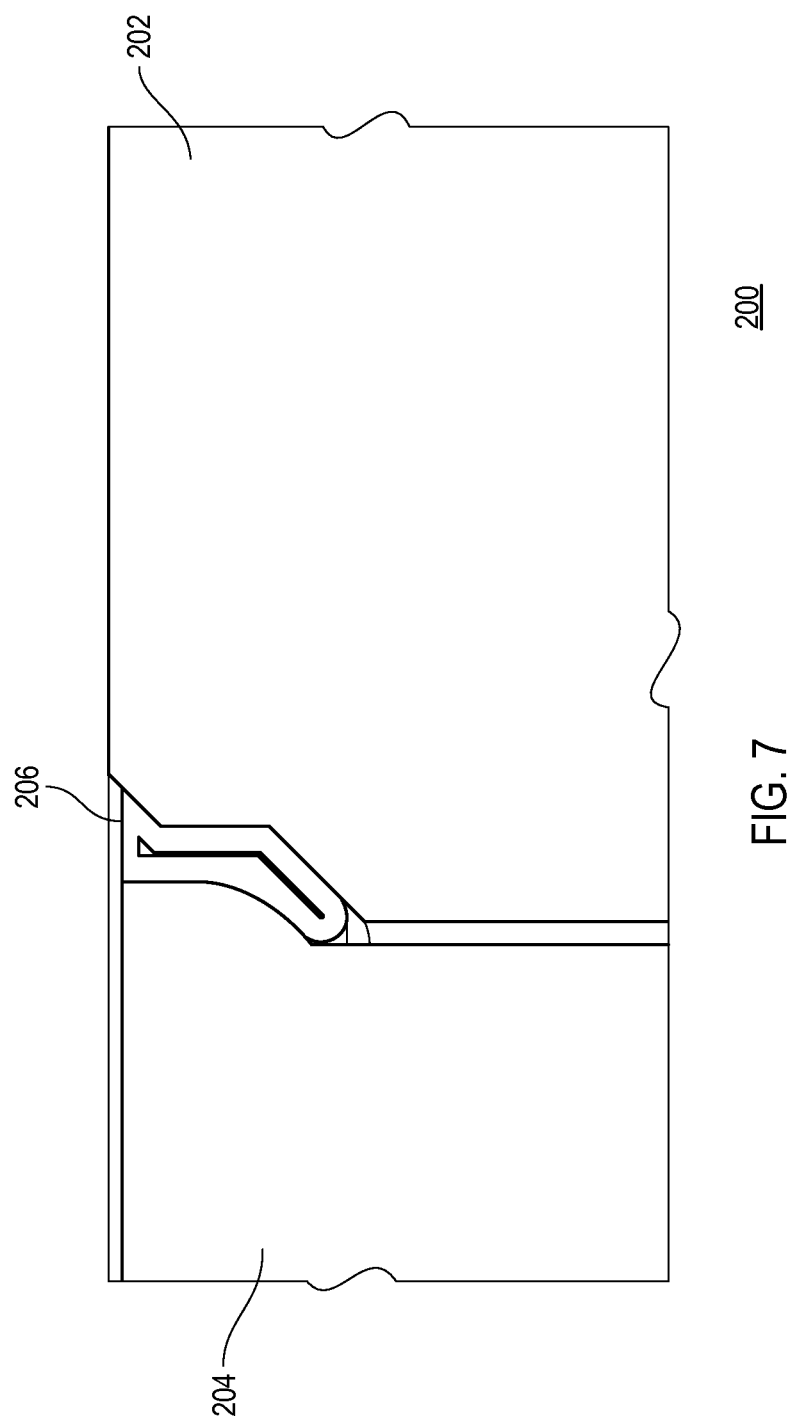

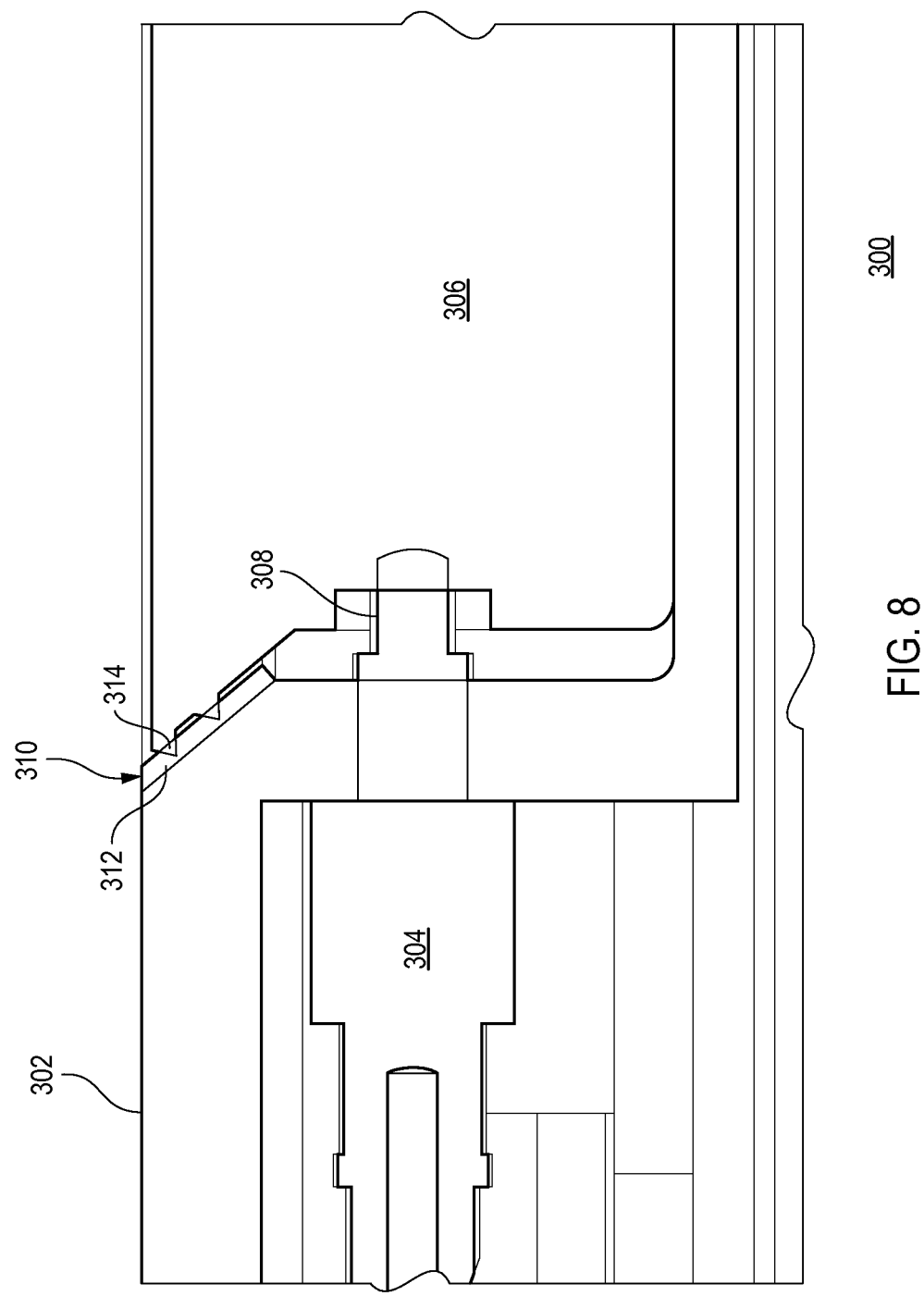

BATTERY PACK WITH INTEGRAL SEAL MEMBER AND ELECTRONIC DEVICE INCLUDING THE SAME

TECHNICAL FIELD

This disclosure relates generally to battery packs and electronic devices powered by the battery packs. In particular, this disclosure relates to a battery pack assembly having an integral seal member for prevention of contaminant ingress into a battery bay in an electronic device.

BACKGROUND

Removable battery packs are widely used with electronic devices to supply electrical power to electrical circuitry in the devices. For instance, a portable X-ray image receptor may include a removable battery pack to supply power to an electrical circuitry for image acquisition. Over time, a battery may die out and need to be removed and replaced. Further, an image receptor may be exposed to human or animal fluids or bio-matter which need to be decontaminated or removed. Typically, the method of cleaning is to wipe the entire receptor panel with disinfectant wipes or other cleaning techniques. In order to prevent the bio-matter and cleaning fluid from entering into the battery bay, which may otherwise cause contamination of the battery contacts and deteriorate performance of the battery and the image receptor, the battery pack is generally sealed from external environment.

In conventional electronic devices including X-ray image receptors, a battery pack is typically held in a receiving module with a removable lid for battery installation and placement. O-ring gaskets are typically used in conjunction with the lid to seal the receiving module from the external environment in order to prevent water and other fluids from entering into the receiving module. The conventional designs may cause improper sealing between the lid and the receiving module, especially after extended or periodic use of the O-ring gaskets and the lid.

Accordingly, there is a need for further development of battery pack assemblies that have improved capability to seal out contaminants from external sources to maximize the performance of the battery and electronic devices powered by the battery.

SUMMARY

Battery pack assembly with an integral sealing gasket is described herein. The gasket allows sealing of the battery pack to the housing of an electronic device to prevent contaminant ingress into the battery bay. The integration of a sealing gasket with a battery pack eliminates the need for a lid removably connectable at a receiving module for the battery pack. The sealing gasket attached to the battery pack, without the aid of a separate lid, can isolate exterior elements such as water, cleaners, dust, dirt, or other contaminants from the interior battery bay and accompanying electrical contacts.

The sealing gasket may be hollow or shaped to provide a seal with the battery bay. The sealing gasket may be constructed from any suitable materials including silicone, thermoplastic elastomers or other chemical resistant sealing materials. The seal may be adhered onto the battery pack. Alternatively, the seal may be a removable device that can be held in place onto the battery pack with a positioning feature on the exterior of the battery pack. The battery pack may be thin-profiled or of any suitable shape and size.

Other embodiments are further described herein.

BRIEF DESCRIPTION OF THE DRAWINGS

These and other features and advantages of the disclosed methods and apparatuses will become better understood upon reading of the following detailed description in conjunction with the accompanying drawings and the appended claims provided below, where:

FIG. 4 is an enlarged perspective view of a portion of a battery pack assembly according to some embodiments of this disclosure;

FIG. 5 is an enlarged cross-sectional view of a portion of a battery pack assembly according to some embodiments of this disclosure;

FIG. 7 is a partial cross-sectional view of an electronic device according to some alternative embodiments of this disclosure; and FIG. 8 is a partial cross-sectional view of an electronic device according to some alternative embodiments of this disclosure.

DETAILED DESCRIPTION

Figure 1:
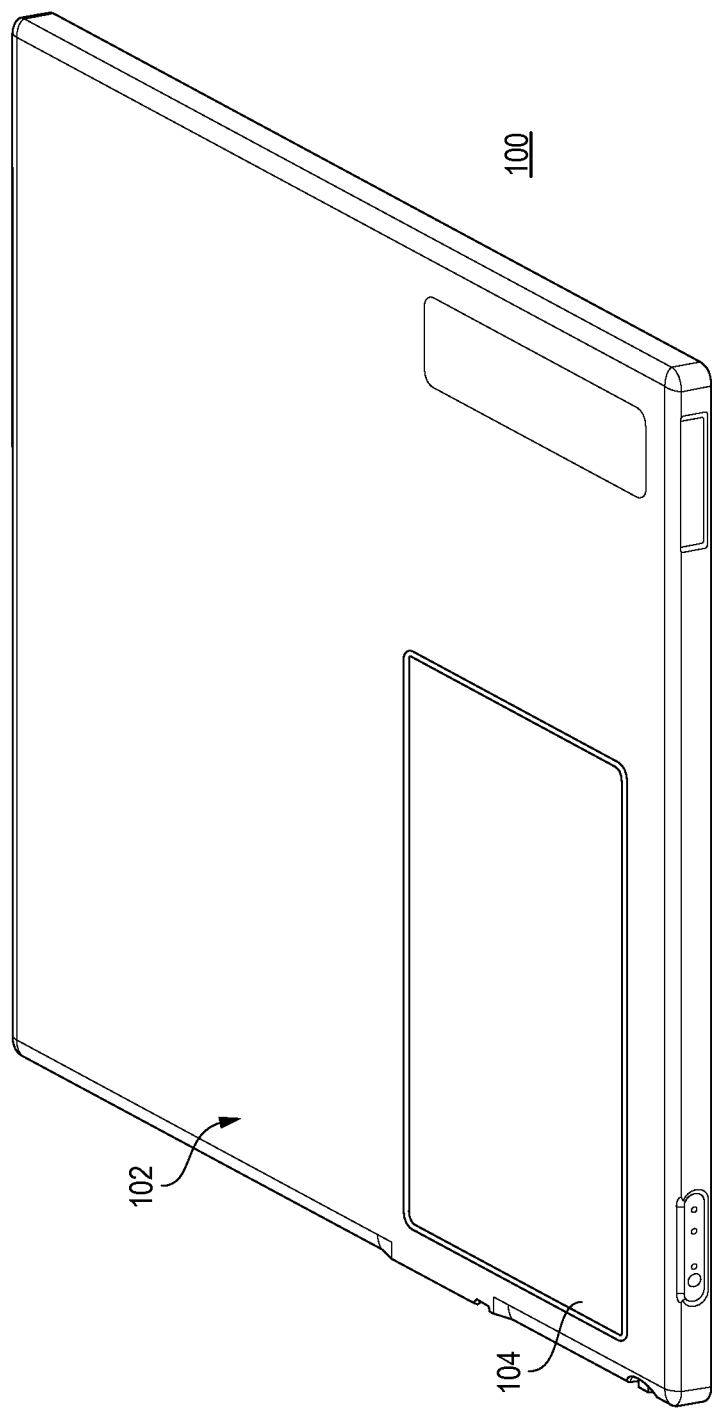
FIG. 1 is a perspective bottom view of a radiographic image receptor including a battery pack according to some embodiments of this disclosure.

Various embodiments of methods and devices for sealing a battery pack to an electronic device are described. It is to be understood that the disclosure is not limited to the particular embodiments described as such may, of course, vary. An aspect described in conjunction with a particular embodiment is not necessarily limited to that embodiment and can be practiced in any other embodiments. For instance, while various embodiments are shown and described in conjunction with a radiographic image receptor, it will be appreciated that the devices and methods described herein can also be used in other electronic devices and applications.

Various relative terms such as "above," "below," "top," "bottom," "height," "depth," "width," and "length," etc. may be used to facilitate description of various embodiments. The relative terms are defined with respect to a conventional orientation of a structure and do not necessarily represent an actual orientation of the structure in manufacture or use. The following detailed description is, therefore, not to be taken in a limiting sense.

As used in the description and appended claims, the singular forms of "a," "an," and "the" may include plural references unless the context clearly dictates otherwise.

As used herein, the term "contaminant" refers to any element or substance that may contaminate the electrical contacts or affect the performance of a battery. A contaminant may include a liquid and solid contaminant such as human or animal fluid, bio-matter, water, cleaning liquid, dirt, or dust etc.

As used herein, the term "thin-profiled battery" refers to any battery that has a thickness dimension less than a maximal linear dimension of its electrical contacts or terminals.

According to this disclosure, a radiographic image receptor may include a housing member having an exterior surface a portion of which defines a recess, an image acquisition assembly contained inside the housing member, a removable battery pack received in the recess in the exterior surface and electrically connected to the image acquisition assembly inside the housing member, and a seal member. The seal member engages the battery pack and the housing member along an outer circumference of the battery pack and an inner circumference of the recess such that the seal member seals the gap between the outer circumference of the battery pack and the inner circumference of the recess, thereby preventing contaminants from an external environment from entering into the interior of the recess through the gap.

The exterior surface of the housing member may include a first surface portion configured to face incident radiation to be detected by the image receptor and a second surface portion opposite to the first surface portion. The recess may be defined in the second surface portion. The recess and the battery pack may be configured such that the battery pack may lay flush with or slightly below the second surface portion.

The housing member may be thin-profiled configured to house an image acquisition assembly that is thin-profiled. As such, the battery pack may also be thin-profiled to power the image acquisition assembly contained inside the housing member.

The seal member may be a gasket seal adhered to the battery pack along an outer circumference of the battery pack. Alternatively, the seal member may be removably attached to the battery pack. As such, the battery pack may include a positioning feature such as a protrusion or ridge structure along the outer circumference of the battery pack, and the seal member may be removably attached to and held in place by the protrusion or ridge structure. The protrusion may be a separate structure, which may be attached to the battery pack housing via various suitable means such as bonding etc. Alternatively, the protrusion may be integral with the battery pack housing, which can be made when the battery pack housing is molded.

The seal member may include a first seal portion and a second seal portion, and the housing member may include a first sealing surface and a second sealing surface each configured to mate with the first and second seal portions of the seal member respectively. The first and second sealing surfaces of the housing member may be non-coplanar with each other, and the seal member may be configured such that when it is compressed against the housing member, the first seal portion engages with the first sealing surface and the second seal portion engages with the second sealing surface.

The seal member may be constructed from any suitable materials, including materials that are resilient, deformable, heat resistant, and/or chemically resistant. Various additives may be blended with the sealing materials to provide desirable properties for the seal members such as self-lubricating properties. In some embodiments, the seal member may be constructed from silicone, thermoplastic elastomers, or other chemical resistant sealing materials.

In some embodiments, a battery pack assembly may include a housing member having an exterior surface, one or more battery cells inside the housing member, and a seal member surrounding a periphery of the housing member, where the seal member is attached to the exterior surface of the housing member. The housing member may include a positioning feature such as a protrusion structure along the periphery, and the seal member may be removably attached to and held in place by the protrusion structure. The protrusion structure and the housing member may be integrally molded. Alternatively, the seal member may be attached to the exterior surface of the housing member by an adhesive. The seal member may be hollow to allow tolerance forgiveness. The sealing member may be constructed from silicone, thermoplastic elastomers, or other chemical resistant sealing materials.

The seal member may include a first seal portion configured to engage with a first sealing surface and a second seal portion configured to engage with a second sealing surface. The first and second sealing surfaces may be non-coplanar with each other.

The battery pack assembly may be thin-profiled and used to power a thin-profiled radiographic image receptor or other electronic devices.

In some embodiments, an electronic device may include a housing member having an exterior surface a portion of which defines a recess, an electronic assembly contained inside the housing member, a removable battery pack received in the recess in the exterior surface and electrically connected to the electronic assembly inside the housing member, and a seal member. The seal member may engage the battery pack and the housing member along an outer circumference of the battery pack and an inner circumference of the recess such that the seal member seals the gap between the outer circumference of the battery pack and the inner circumference of the recess, thereby preventing contaminants from an external environment from entering into the interior of the recess through the gap.

The electronic assembly may be an image acquisition assembly that is configured and constructed to detect incident radiation and generate signals for image reconstruction and processing. The electronic assembly may also be other electronic components including an electronic circuit such as an analog or a digital circuit. Exemplary electronic devices include, but are not limited to, computers including laptops and tablets, cameras, camcorders, radios, phones including mobile phones and smart phones, scanners, remote controls, DVD or Blu-ray players, and any other electronic devices that can be powered by a removable battery pack.

The seal member may be a gasket seal adhered to the battery pack along an outer circumference of the battery pack. Alternatively, the seal member may be removably attached to the battery pack. As such, the battery pack may include a positioning feature such as a protrusion or ridge structure along the outer circumference of the battery pack, and the seal member may be removably attached to and held in place by the protrusion or ridge structure. The protrusion or ridge may be a separate structure, which may be attached to the battery pack housing via various suitable means such as bonding etc. Alternatively, the protrusion or ridge may be integral with the battery pack housing, which can be made when the battery pack housing is molded.

The seal member may include a first seal portion and a second seal portion, and the housing member may include a first sealing surface and a second sealing surface each configured to mate with the first and second seal portions of the seal member respectively. The first and second sealing surfaces of the housing member may be non-coplanar with each other, and the seal member may be configured such that when it is compressed against the housing member, the first seal portion engages with the first sealing surface and the second seal portion engages with the second sealing surface.

The seal member can be constructed from any suitable materials, including materials that are resilient, deformable, or chemically resistant. Various additives may be blended with the materials to provide desirable properties for the seal members such as self-lubricating properties. In some embodiments, the sealing member may be constructed from silicone, thermoplastic elastomers, or other chemical resistant sealing materials.

Exemplary embodiments will now be described with reference to the figures. It should be noted that some figures are not drawn to scale. The figures are only intended to facilitate the description of specific embodiments and are not intended as an exhaustive description or as a limitation on the scope of the invention.

Figure 2:
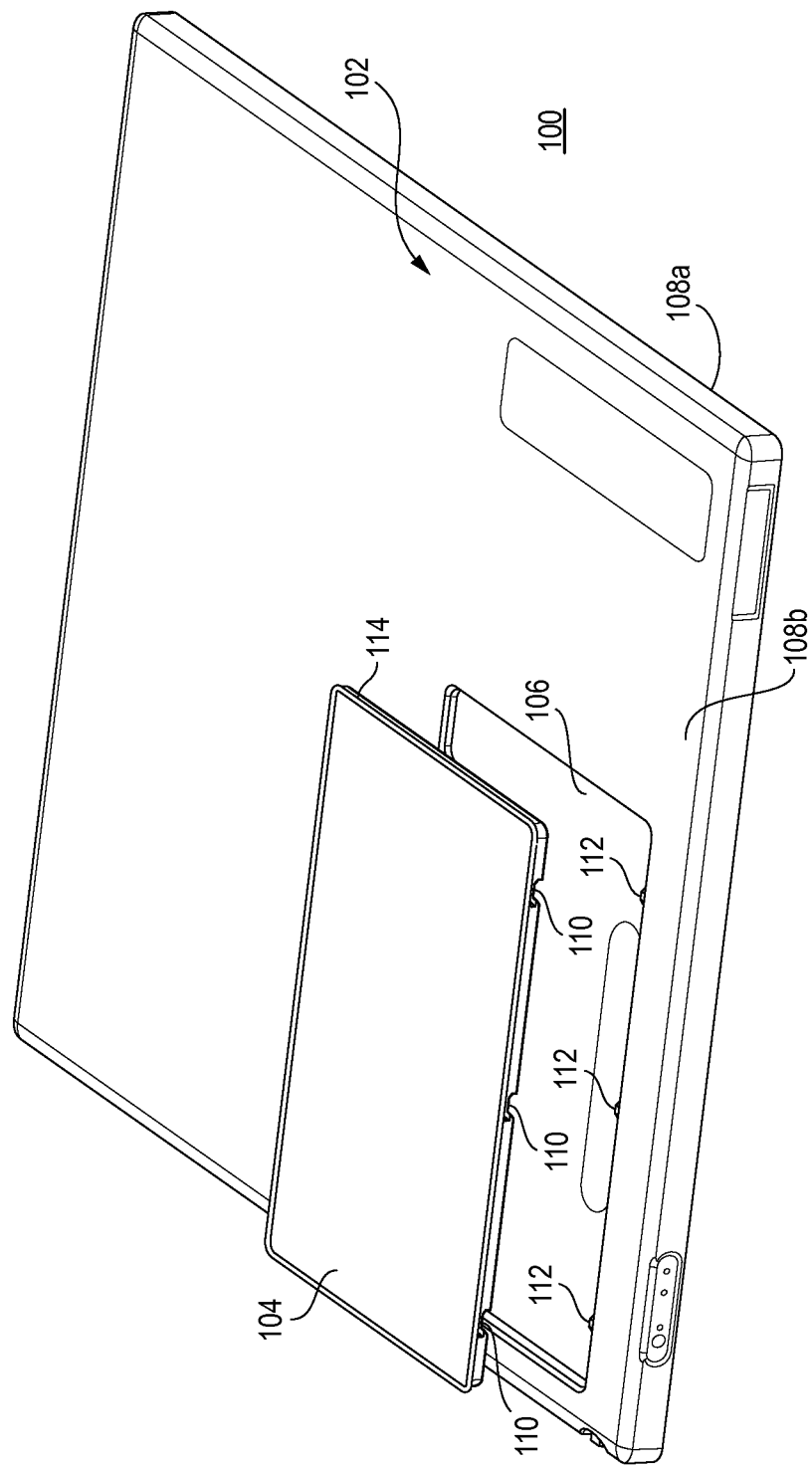
FIG. 2 is a perspective exploded view of a radiographic image receptor showing a battery pack and a battery bay in the receptor housing according to some embodiments of this disclosure.
Figure 3:
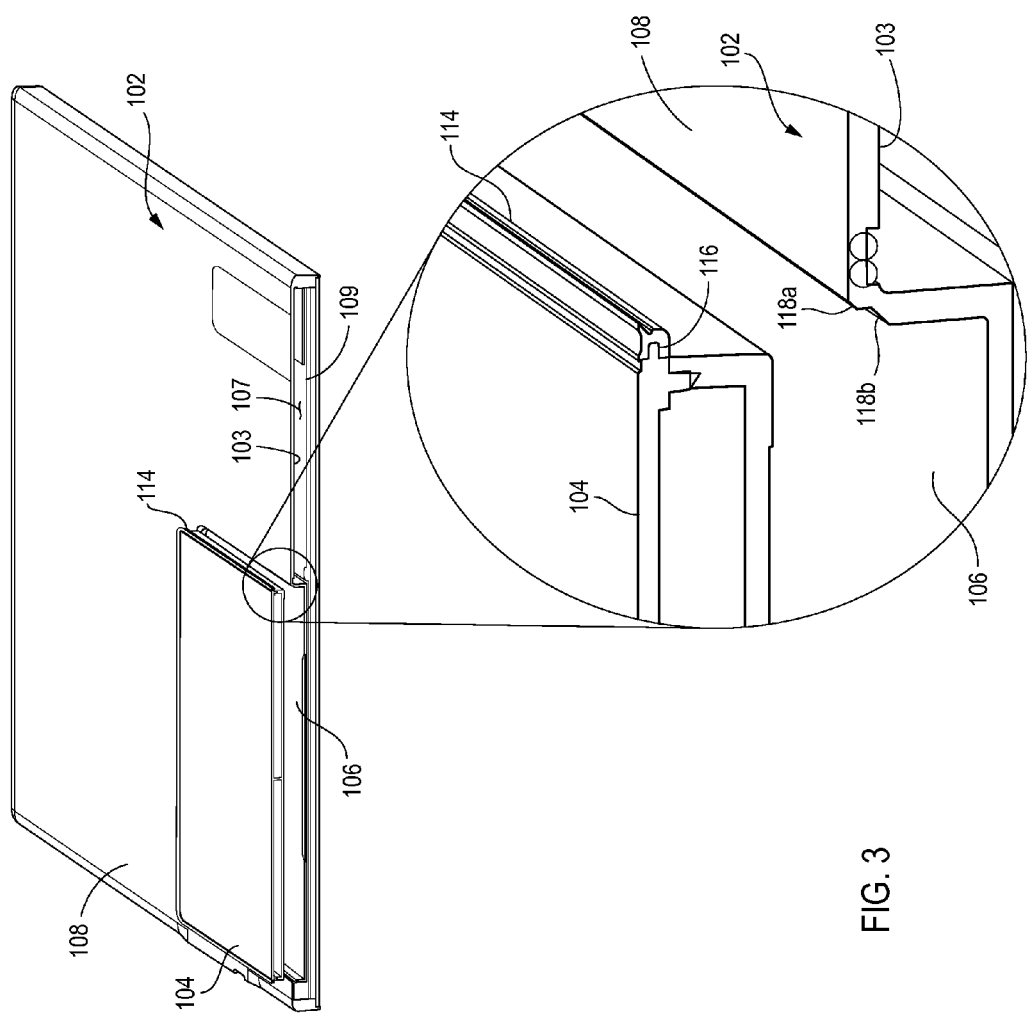
FIG. 3 is an exploded cut-away view of a radiographic image receptor showing some details of the battery bay and the battery pack according to some embodiments of this disclosure.

Referring to FIGS. 1 and 2, an exemplary radiographic image receptor including a removable battery pack will be described. FIG. 1 is a perspective bottom view of an image receptor 100 showing a housing member 102 and a battery pack 104 located outside of the housing member 102. The housing member 102 has an interior surface 103 (FIG. 3) and an exterior surface 108. The interior surface 103 of the housing member 102 defines an interior compartment 107 in which an image acquisition assembly 109 may be contained (FIG. 3). A portion of the exterior surface 108 defines a recess 106 in which a removable battery pack 104 may be received. FIG. 2 is an exploded view of the image receptor 100 showing a battery bay or recess 106 in the exterior surface of the housing member 102 and a battery pack 104 received in the battery bay 106. As shown in FIGS. 1 and 2, the image receptor 100 includes a housing member 102, which may be configured to house an image acquisition assembly 109 (FIG. 3) inside. The image acquisition assembly 109 may include an electrical circuitry or circuitries that is or are configured and constructed to detect incident radiation and generate signals for image reconstruction and processing. The image acquisition assembly 109 may be electrically coupled to and powered by the battery pack 104 which may be located outside the housing 102. Constructions of image acquisition assemblies are known in the art and therefore their detail description is omitted herein to avoid obscuring the description of various embodiments of this disclosure. U.S. Pat. No. 6,800,858 issued on Oct. 5, 2004 entitled "X-ray Image Acquisition Apparatus," which is assigned to Varian Medical Systems, Inc., describes various embodiments of X-ray image acquisition assemblies. The disclosure of U.S. Pat. No. 6,800,858 is incorporated herein by references in its entirety. It should be noted the inventive principles of this disclosure may apply to any electronic devices that may be powered by a removable battery pack.

In some embodiments, the housing member 102 may be thin-profiled configured to house an image acquisition assembly that is thin-profiled. As such, the battery pack 104 may also be thin-profiled to power the image acquisition assembly contained inside the housing member 102. It should be noted that inventive principles described in this disclosure are not limited to thin-profiled image receptor and/or battery pack. Further, constructions of various battery packs are known in the art and therefore their detail description is omitted herein to avoid obscuring the description of various embodiments of this disclosure.

The housing member 102 includes an exterior surface 108. The exterior surface 108 may include a first surface portion 108a configured to face incident radiation to be detected by the image receptor 100 and a second surface portion 108b opposite to the first surface portion 108a. In the second surface portion 108b, a battery bay or a recess 106 may be defined to receive and hold the battery pack 104. The battery pack 104 may be secured in the battery bay 106 by any suitable mechanisms. By way of example, slots or pockets 110 may be provided in the battery pack 104 and complimentary protrusions 112 may be provided in the housing member 102 (FIG. 2). In use, the pockets 110 in the battery pack 104 may slidably engage with the protrusions 112 in the housing member 102 to secure the battery pack 104 in the battery bay 106, or the pockets 110 may slidably disengage with the protrusions 112 to remove the battery pack 104 from the battery bay 106. Other mechanisms such as latches, locks etc. may also be used to secure the battery pack 104 in the battery bay 106. Once being held or secured in the battery bay 106, the battery pack 104 may lay substantially flush with the second surface portion 108b or slightly below the second surface portion 108b.

A seal member 114 may seal the gap between the battery pack 104 and the housing member 102 in the battery bay area. Because the battery pack 104 may be removable for replacement, a gap may exist between the battery pack 104 and the housing member 102 along the outer circumference of the battery pack 104 and the inner circumference of the battery bay 106. If proper sealing is not provided, contaminants such as human or animal fluids, bio-matter, or other contaminants may enter the battery bay 106 when the image receptor 100 is in use. Water or cleaning liquids may also enter the battery bay 106 when the image receptor 100 is cleaned. These contaminants may cause contamination of the battery contacts and deteriorate performance of the battery and image receptor. The seal member 114 may engage the battery pack 104 and the housing member 102 along the outer circumference of the battery pack 104 and the inner circumference of the battery bay 106 such that the seal member 114 seals the gap, thereby preventing external contaminants from entering into the battery bay 106 through the gap.

Figure 6:
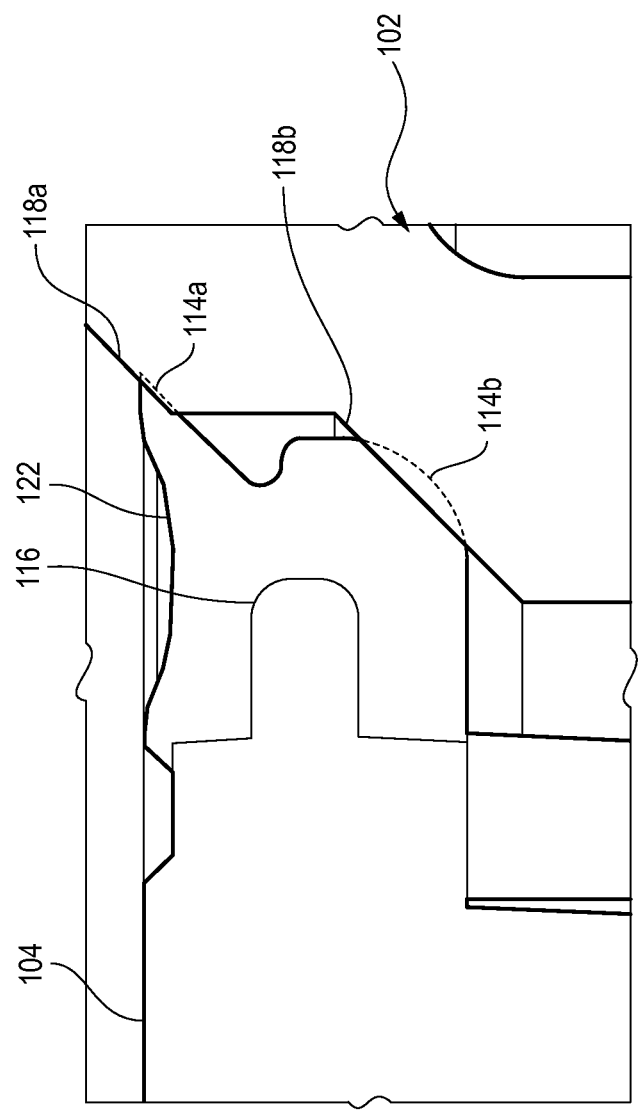
FIG. 6 is an enlarged cross-sectional view showing a seal member engaging with a battery pack and an image receptor housing member according to some embodiments of this disclosure.

Referring to FIGS. 3-6, an exemplary seal member 114 for sealing a battery pack 104 to a housing member 102 will be described in greater detail. FIG. 3 is an exploded cut-away view of an image receptor 100 showing some details of a battery pack 104 with an integral seal member 114 and sealing surfaces 118a, 118b in a housing member 102. FIG. 4 is an enlarged view of a portion of a battery pack assembly showing some details of the shape of a seal member 114. FIG. 5 is an enlarged cross-sectional view of a portion of a battery pack assembly showing some further details of a seal member 114 removably attached to and held in place by a protrusion support 116 on the battery pack 104. FIG. 6 is an enlarged cross-sectional view showing a seal member 114 attached to a battery pack 104 and compressed against the sealing surfaces 118a, 118b in a housing member 102.

As shown in FIGS. 3-6, the seal member 114 may be a gasket seal adhered to the battery pack 104 along an outer circumference of the battery pack 104. Alternatively, the seal member may be removably attached to the battery pack 104. As such, the battery pack 104 may include a positioning feature such as a protrusion or ridge structure 116 along the outer circumference of the battery pack 104. The seal member 114 may include a groove configured to mate the protrusion structure 116 so that the seal member 114 can be removably attached to and held in place by the protrusion or ridge structure 116. The protrusion 116 may be a separate structure, which may be attached to the battery pack housing via various suitable means such as bonding etc. Alternatively, the protrusion 116 may be integrally molded with the battery pack housing, which can be made when the battery pack housing is constructed.

The seal member 114 can be constructed from any suitable materials, including sealing materials that are resilient, deformable, and/or chemically resistant. The sealing material may be selected to prevent ingress of contaminants such as human or animal fluids or bio-matters, water, or cleaning liquids etc. Various additives may be blended with the materials to provide desirable properties for the seal member such as self-lubricating properties. By way of example, the seal member 114 may be constructed from a material comprising silicone, thermoplastic elastomers, or other sealing materials known in the art.

The seal member 114 may be shaped to have a configuration that matches a circumferential configuration of the battery pack 104. For example, the seal member 114 may be shaped to have a generally circular, rectangular, oval, or other configuration, or any combination thereof. In some embodiments, the seal member 114 may have two or more circumferential seal portions 114a, 114b configured to engage with two or more sealing surfaces 118a, 118b in the housing member 102 (FIGS. 5 and 6). For example, the battery bay 106 in the housing member 102 may be configured to provide a first sealing surface 118a and a second sealing surface 118b each along the circumference of the battery bay opening. The first and second circumferential seal portions 114a, 114b of the seal member 114 may each mate with the first and second circumferential sealing surfaces 118a, 118b respectively, providing primary and secondary sealing. The first and second sealing surfaces 118a, 118b may be non-coplanar with each other. As such, the first and second seal portions 114a, 114b of the seal member 114 may be configured so that when the seal member 114 is compressed against the housing member 102, the first seal portion 114a may engage with the first sealing surface 118a and the second seal portion 114b engage with the second sealing surface 118b respectively to provide tight sealing. In FIG. 6, the dotted lines overlapping the sealing surfaces 118a, 118b show that the first and second seal portions 114a, 114b of the seal member 114 can be deformed from their original shape when the seal member 114 is compressed against the sealing surfaces 118a, 118b to allow for tolerance stack-up.

The particular shape and configuration of the seal member 114 shown in FIGS. 3-6 is provided for illustration purpose. As shown, the seal member 114 may include a flexible lip portion 114a extended outwardly and a rounded or curved portion 114b. Between the lip portion 114a and the rounded portion 114b may be a cut-out or void space 120, which may allow for flexibility of the lip portion 114a. The top surface 122 of the seal member 114 may be recessed to provide for more flexibility of the lip portion 114a. When the seal member 114 is attached to the battery pack 104 and compressed against the housing member 102, the flexible lip portion 114a may engage with a first sealing surface 118a to provide for primary sealing, and the rounded portion 114b may engage with a second sealing surface 118b to provide for secondary sealing. One of ordinary skill in the art will appreciate that various modifications can be made with respect to the shape and configuration of the seal member 114, and the scope of the present claims is not limited to the particular shape and configuration shown. In some embodiments, the first and second seal portions 114a, 114b may be formed in a single piece of a sealing material.

Referring to FIGS. 7 and 8, some alternative embodiments of this disclosure will be described. FIG. 7 illustrates an electronic device 200 which may include a housing member 202 enclosing an electronic assembly (not shown), and a battery pack 204 located outside the housing 202 and supplying power to the electronic assembly inside the housing 202.

The electronic assembly (not shown) contained inside the housing member 202 may be any electronic components that include an electronic circuitry such as an analog or a digital circuit. By way of example, the electronic device 200 may be a radiographic image receptor, a computer such as a laptop and tablet, a camera, a camcorder, a radio, a phone such as a mobile phone and smart phone, a scanner, a remote control, a DVD or Blu-ray player, and any other electronic device that can be powered by a removable battery pack. As shown in FIG. 7, the gap between the removable battery pack 204 and the housing member 202 may be sealed by a seal member 206. The seal member 206 may be bonded to an outer circumference of the battery pack 204 and compressed against the housing member 202 when in use. Alternatively, the seal member 206 may be bonded to the housing member 202 and compressed against by the battery pack 204 when in use. The seal member 206 may be disposed along the edge portion of the battery pack 204, and thus may additionally serve as a bumper to protect the battery 204 from damages. The seal member 206 may be hollow to allow for tolerance forgiveness.

FIG. 8 illustrates an electronic device 300 which may include a housing member 302 enclosing an electronic assembly 304 inside, and a battery pack 306 located outside the housing 302 and supplying power to the electronic assembly 304. A portion of the exterior surface of the housing member 302 may define a recess in which a removable battery pack 306 may be received and secured. The electronic assembly 304 contained inside the housing 302 may be electrically connected to the battery 306 via a connector such as pogo pin connector 308. The gap between the removable battery pack 306 and the housing member 302 may be sealed by a seal member 310. The seal member 310 may include a silicone gasket 312, which may be bonded to a circumference in the battery bay opening in the housing member 302, and sealing lips or protrusions 314, which may be attached to the battery pack 306. The sealing tips or protrusions 314 may be compressed against the silicone gasket 312 when in use, thereby providing sealing for the battery pack 306 to the housing member 302.

Exemplary embodiments of a battery pack assembly and electronic devices including the battery pack assembly are described. Those skilled in the art will appreciate that various modifications may be made within the spirit and scope of the disclosure. All these or other variations and modifications are contemplated by the inventors and within the scope of the disclosure.

What is claimed is:

1. A radiographic image receptor, comprising:
    a housing member having an interior surface and an exterior surface, the interior surface defining an interior compartment and a portion of the exterior surface defining a recess;
    an x-ray image acquisition assembly contained in the interior compartment;
    a removable battery pack received in the recess and electrically connected to the x-ray image acquisition assembly; and
    a seal member engaging the battery pack and the housing member along an outer circumference of the battery pack and an inner circumference of the recess such that the seal member seals a gap between the outer circumference of the battery pack and the inner circumference of the recess, wherein the seal member is integrated to the battery pack or the housing member.

2. The radiographic image receptor of claim 1 wherein the exterior surface of the housing member comprises a first surface portion configured to face incident radiation and a second surface portion opposite to the first surface, and wherein the recess is defined in the second surface portion.

3. The radiographic image receptor of claim 2 wherein the battery pack and the recess are configured such that the battery pack lays substantially flush with or below the second surface portion.

4. A radiographic image receptor, comprising:
a housing member having an exterior surface, a portion of the exterior surface defining a recess;
an x-ray image acquisition assembly contained inside the housing member;
a removable battery pack received in the recess in the exterior surface and electrically connected to the x-ray image acquisition assembly inside the housing member; and
a seal member engaging the battery pack and the housing member along an outer circumference of the battery pack and an inner circumference of the recess such that the seal member seals a gap between the outer circumference of the battery pack and the inner circumference of the recess, wherein the seal member is integrated to the battery pack or the housing member;
wherein the battery pack has a thickness dimension less than a maximal linear dimension of its electrical contacts.

5. The radiographic image receptor of claim 1 wherein the seal member is integrated to the battery pack by an adhesive.

6. The radiographic image receptor of claim 1 wherein the battery pack comprises a protrusion structure along the outer circumference of the battery pack, and the seal member is integrated to the battery pack by attaching the seal member to the protrusion structure.

7. The radiographic image receptor of claim 1 wherein the seal member is integrated to the housing member by an adhesive.

8. The radiographic image receptor of claim 1 wherein the seal member is hollow.

9. The radiographic image receptor of claim 1,
wherein the inner circumference of the recess comprises a circumferential first sealing surface and a circumferential second sealing surface that is non-coplanar with the first sealing surface; and
wherein the seal member comprises a circumferential first seal portion configured to engage with the first sealing surface and a circumferential second seal portion configured to engage with the second sealing surface.

10. The radiographic image receptor of claim 1 wherein the seal member is constructed from a material comprising silicone or a thermoplastic elastomer.

11. A battery pack assembly, comprising:
a housing member having an exterior surface;
one or more battery cells inside the housing member; and
a seal member surrounding a periphery of the housing member, wherein the seal member is attached to the exterior surface of the housing member.

12. The battery pack assembly of claim 11 wherein the housing member comprises a protrusion structure along the periphery and the seal member is removably attached to and held in place by the protrusion structure.

13. The battery pack of claim 12 wherein the protrusion structure and the housing member are integrally molded.

14. The battery pack assembly of claim 11 wherein the seal member is attached to the exterior surface of the housing member by an adhesive.

15. The battery pack assembly of claim 11 wherein the seal member is hollow.

16. The battery pack assembly of claim 11 wherein the seal member comprises a circumferential first seal portion configured to engage with a circumferential first sealing surface and a circumferential second seal portion configured to engage with a circumferential second sealing surface that is non-coplanar with the first sealing surface.

17. A battery pack assembly, comprising:
a housing member having an exterior surface;
one or more battery cells inside the housing member; and
a seal member surrounding a periphery of the housing member, wherein the seal member is attached to the exterior surface of the housing member,
wherein the one or more battery cells and the housing member are thin-profiled such that a combination of the battery cells and the housing member has a thickness dimension less than a maximal linear dimension of electrical contacts of the battery pack assembly.

18. The battery pack assembly of claim 11 wherein the seal member is constructed from a material comprising silicone or a thermoplastic elastomer.

19. An electronic device, comprising:
a housing member having an interior surface and an exterior surface, the interior surface defining an interior compartment and a portion of the exterior surface defining a recess;
an electronic assembly contained in the interior compartment;
a battery pack received in the recess and electrically connected to the electronic assembly inside the housing; and
a seal member engaging the battery pack and the housing member along an outer circumference of the battery pack and an inner circumference of the recess such that the seal member seals a gap between the outer circumference of the battery pack and the inner circumference of the recess, wherein the seal member is integrated to the battery pack or the housing member.

20. The electronic device of claim 19 wherein the battery pack comprises a protrusion structure along the outer circumference of the battery pack, and the seal member is integrated to the battery pack by attaching the seal member to the protrusion structure.

21. The electronic device of claim 19,
wherein the inner circumference of the recess comprises a circumferential first sealing surface and a circumferential second sealing surface that is non-coplanar with the first sealing surface; and
wherein the seal member comprises a circumferential first seal portion configured to engage with the first sealing surface and a circumferential second seal portion configured to engage with the second sealing surface.

22. The electronic device of claim 19, wherein the battery pack has a thickness dimension less than a maximal linear dimension of its electrical contacts.

* * * * *